United States Patent [19]
Gey et al.

[11] 3,950,324
[45] Apr. 13, 1976

[54] D-GLUCOSE-1-0-NICOTINOYL-2-DEOXY-2-NICTINAMIDO DERIVATIVES

[75] Inventors: Karl Friedrich Gey, Reinach; Joseph Kiss, Arlesheim; Hans Lengsfeld, Reinach; Pierre-Charles Wyss, Muttenz; Willy Schuep, Birsfelden, all of Switzerland

[73] Assignee: Hoffmann-La Roche Inc., Nutley, N.J.

[22] Filed: Jan. 9, 1975

[21] Appl. No.: 539,886

[30] Foreign Application Priority Data
Jan. 25, 1974 Switzerland.......................... 1039/74
Nov. 14, 1974 Switzerland........................ 15193/74

[52] U.S. Cl...... 260/211 R; 260/210 R; 260/234 R; 424/180
[51] Int. Cl.².......................................... C07H 5/06

[58] Field of Search......... 260/234 R, 210 R, 211 R

[56] References Cited
UNITED STATES PATENTS
2,918,462   12/1959   Druey et al. .................... 260/211 R OTHER PUBLICATIONS
Krueger et al., Chem. Abst. Vol. 66, 1967, p. 2715, y.

*Primary Examiner*—Johnnie R. Brown
*Attorney, Agent, or Firm*—Samuel L. Welt; Jon S. Saxe; George M. Gould

[57]    ABSTRACT
A novel class of glucose derivatives, i.e., 3,4,6-tri-o-acyl-2-deoxy-2-nicotinamido-1-0-nicotinoyl-D-glucopyranoses are disclosed. These compounds are pharmaceutically active and are useful as plasma lypid lowering agents.

6 Claims, No Drawings

D-GLUCOSE-1-0-NICOTINOYL-2-DEOXY-2-NICTINAMIDO DERIVATIVES

PRIOR ART

The compound 2-acetamido-2-deoxy-D-glucopynanose-6-nicotinate is disclosed in Japanese Pat. No. 4734366.

BRIEF DESCRIPTION OF THE INVENTION

The present invention relates to glucose derivatives. The glucose derivatives provided by the present invention have the following general formula

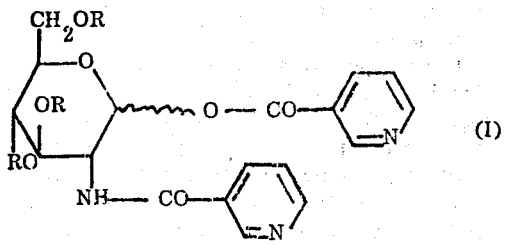

wherein R is lower alkanoyl, (lower alkoxy)-(lower alkanoyl) or aroyl.

The aforementioned lower alkanoyl groups contain up to 6 carbon atoms. Examples of such groups are acetyl, propionyl and the like. The lower alkoxy groups contain up to 6 carbon atoms. Examples of such groups are methoxy, ethoxy and the like. Examples of aroyl groups are benzoyl groups which may be substituted by $C_1-C_6$ alkyl and/or $C_1-C_6$ alkoxy and/or halogen.

The glucose derivatives of formula I can be present in two different anomeric forms ($\alpha$ and $\beta$) of the formulae

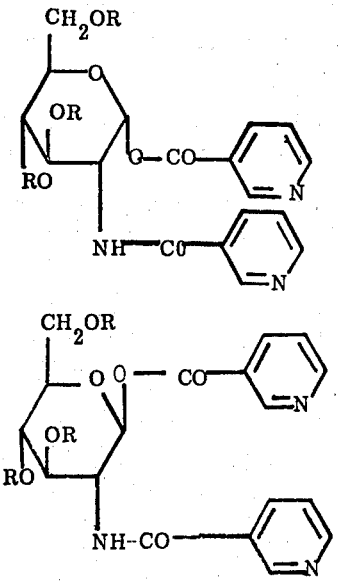

wherein R is as above. The $\beta$ form is preferred.

Also preferred are glucose derivatives of formula I in which R is acetyl.

Examples of glucose derivatives of formula I are:
3,4,6-tri-O-acetyl-2-deoxy-2-nicotinamido-1-O-nicotinoyl-$\beta$,D-glucopyranose,
3,4,6-tri-O-propionyl-2-deoxy-2-nicotinamido-1-O-nicotinoyl-$\beta$,D-glucopyranose, and
3,4,6-tri-O-benzoyl-2-deoxy-2-nicotinamido-1-O-nicotinoyl-$\beta$,D-glucopyranose.

The glucose derivatives of formula I are conveniently prepared by replacing the substituent denoted by X in a compound of the general formula

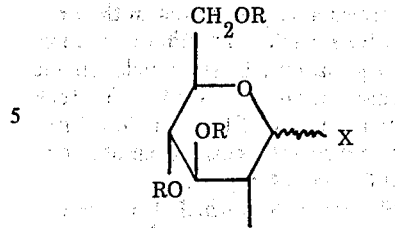

wherein X is halogen, hydroxy, or protected hydroxy and R is as above, and wherein, in the case where X is halogen, said compound can be present in the form of the corresponding oxazolinium halide, by the nicotinoyloxy group in a manner known per se.

The halogen atom denoted by X in formula II hereinbefore can be a chlorine, bromine, fluorine or iodine atom. A chlorine or bromine atom is preferred.

A protected hydroxy group denoted by X in formula II hereinbefore can be lower alkoxy, aryloxy, acyloxy or a group of the formula —O—Z in which Z is a heterocyclic group (e.g. imidazolyl).

An acyloxy group denoted by X in formula II hereinbefore can be a lower alkanoyloxy, alkoxyalkanoyloxy or aroyloxy group of the formula —O—R in which R is as above. An acyloxy group denoted by X can also be a (lower alkanoyloxy or aroyloxy)-carbonyloxy group.

The replacement of the substituent denoted by X in a compound of formula II by the nicotinoyloxy group can be carried out by reaction with a nicotinic acid derivative.

Thus, for example, a compound of formula II in which X represents a halogen atom or a protected hydroxy group can be reacted with an organic nicotinic acid salt (e.g. a polyalkylammonium salt such as the triethylamine or tetrabutylammonium salt).

This reaction can conveniently be carried out in an organic solvent (e.g. acetonitrile, dimethyl sulphoxide, dimethylformamide, a nitroalkane, a halogenated hydrocarbon or the like) at a temperature between about 0°C and the reflux temperature of the reaction mixture.

A compound of formula II in which X represents an (alkanoyloxy or aroyloxy)-carbonyloxy group can be reacted with nicotinic acid or a derivative thereof (e.g. a halide).

This reaction is conveniently carried out in the presence of a solvent (e.g. dimethyl sulphoxide, acetonitrile or the like) at a temperature between 50°C and the reflux temperature of the reaction mixture.

A compound of formula II in which X represents a free hydroxy group can be reacted with a nicotinic acid derivative (e.g. a nicotinic acid halide, nicotinic acid azide or nicotinic acid anhydride).

This reaction can conveniently be carried out at a temperature between −10°C and 50°C and in the presence of a condensation agent (e.g. pyridine or triethylamine).

The compounds of formula II are known or can be prepared in a manner known per se.

Thus, a compound of formula II in which X represents a halogen atom can be prepared by reacting N-nicotinoyl-D-glucosamine with an appropriate acyl halide of the general formula

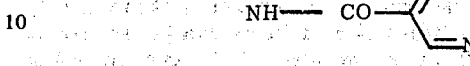

wherein X is halogen and R is as above.

This reaction is conveniently carried out in the presence of an organic solvent such as an ether (e.g. dioxane), a nitroalkane (e.g. nitromethane), a halogenated hydrocarbon (e.g. chlorocorm) or the like. The temperature is not a critical feature of this reaction. However, this reaction is conveniently carried out at a temperature between 50°C and 100°C.

The compounds of formula II in which X represents a halogen atom, namely the compounds of formula II$_a$ hereinafter in which X is halogen, can be present in ionized form, i.e. in the form of the corresponding oxazolinium halides of formula II$_b$ hereinafter.

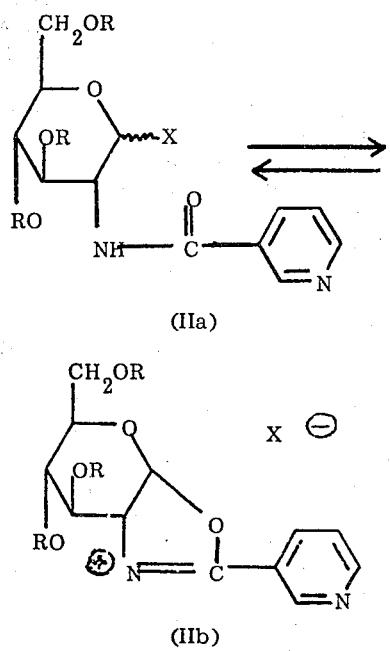

(IIa)

(IIb)

An equilibrium exists between the compounds of formulae II$_a$ and II$_b$ from which the compound of formula II$_a$ or II$_b$ can be isolated if desired.

A compound of formula II in which X represents a hydroxy group can be prepared by hydrolysing a corresponding compound of formula II in which X represents a halogen atom.

The hydrolysis is carried out in the presence of a small amount of water, conveniently in the presence of an organic solvent (e.g. an ether, a nitroalkane, an aromatic hydrocarbon or the like) at a temperature between −30°C and room temperature.

A compound of formula II in which X represents an acyloxy group can be prepared by reacting the corresponding 1,3,4,6-tetra-O-acyl-D-glucosamine with nicotinic acid or a derivative thereof (e.g. the anhydride, a halide or an activated ester such as the p-nitrophenyl ester).

The reaction is conveniently carried out in the presence of a condensation agent (e.g. pyridine). The temperature is not a critical feature of this reaction, but the reaction is conveniently carried out at a temperature between 50°C and 100°C.

A compound of formula II in which X represents a lower alkoxy group can be prepared by the catalyzed reaction of N-nicotinoyl-D-glucosamine with a corresponding lower alkanol followed by acylation in the 3-,4- and 6-position of the resulting compound which is lower alkoxylated in the 1-position.

As the catalyst there can be used an acid (e.g., hydrochloric acid or sulfuric acid), a Lewis acid (e.g., zinc chloride), a cation exchange resin or the like. The lower alkoxylation can be carried out at a temperature between 50°C. and the reflux temperature of the reaction mixture.

The acylation can be carried out using an appropriate acyl halide, anhydride or azide. When an acyl halide or an azide is used, the acylation is carried out in the presence of a tertiary base (e.g., pyridine, trimethylamine or the like). When an anhydride is used, the acylation is carried out in the presence of an alkali metal salt of the corresponding acid in anhydrous form and conveniently in the presence of an excess of anhydride. The acylation can be carried out at a temperature between 0°C. and 100°C. in both of the foregoing procedures.

A compound of formula II in which X represents an aryloxy group can be prepared, for example, by reacting a corresponding N-nicotinoyl-1,3,4,6-tetra-O-acyl-glucosamine with a corresponding phenol in the presence of one of the aforementioned acid catalysts.

A compound of formula II in which X represents an (alkoxy or aryloxy)-carbonyloxy group can be prepared by reacting a corresponding compound of formula II in which X represents a hydroxy group with a corresponding halocarbonic acid ester.

The glucose derivatives of formula I have a plasma lipid-lowering activity. An advantageous property of these glucose derivatives lies in the slow cleavage of nicotinic acid therefrom, which leads to a long-lasting increase of the nicotinic acid concentration in the plasma. From this there results a long-lasting reduction of the lipids in the plasma. Thus, after a single administration of 3,4,6-tri-O-acetyl-2-deoxy-2-nicotinamido-1-O-nicotinoyl-β,D-glucopyranose to rats, the lowering of the triglyceride level in the plasma persists over 13 hours. The toxicity (LD$_{50}$) of this glucose derivative in rats amounts to over 6000 mg/kg determined in the tenth day after five oral administrations.

The glucose derivatives of formula I are conveniently administered in an amount of about 10 to 100 mg/kg. daily.

The aforementioned dosages are, however, only given by way of example and can be varied upwards or downwards according to the special circumstances present or dosage forms administered.

The pharmaceutical preparations provided by the present invention contain a glucose derivative of formula I hereinbefore in association with a compatible pharmaceutical carrier. Such pharmaceutical preparations can be produced by mixing a glucose derivative of formula I as the essential active ingredient with non-toxic, inert solid or liquid carriers suitable for therapeutic administration and customary in pharmaceutical preparations.

Examples of such carriers are water, gelatin, gum arabic, lactose, starch, magnesium stearate, talc, vegetable oils, polyalkyleneglycols, petroleum jelly, etc. The pharmaceutical preparations can be made up in solid form (e.g., as tablets, dragees, suppositories or capsules) or in liquid form (e.g., as solutions, suspensions or emulsions). The pharmaceutical preparations may be sterilized and/or may contain adjuvants such as preserving, stabilizing, wetting or emulsifying agents, salts for variation of the osmotic pressure or buffers. They can also contain other therapeutically valuable substances.

A preferred dosage form comprises tablets containing about 100 mg. to 1000 mg. of a glucose derivative of formula I.

The following examples are illustrative but not limitative of the present invention.

EXAMPLE 1

2 G. of 2-deoxy-2-nicotinamido-1,3,4,6-tetra-O-acetyl-β,D-glucopyranose are dissolved in 50 ml. of methylene chloride and treated with 2 ml. of acetyl chloride. Hydrogen chloride is introduced into this solution while stirring for 1 hour. The solution is left to stand in a refrigerator for 48 hours, then added to 100 ml. of ice-water and neutralized with 2N sodium carbonate solution. The organic phase is separated, dried over magnesium sulfate and evaporated. The residue is dissolved in 30 ml. of acetonitrile, treated with a solution of triethylammonium nicotinate (prepared from 0.65 g. of nicotinic acid and 20 ml. of triethylamine) in 20 ml. of acetonitrile and stirred overnight. The mixture is evaporated, taken up in 100 ml. of chloroform and washed three times with 50 ml. of water. The organic phase is separated, dried over sodium sulfate, evaporated and the residue crystallized from ethanol. There is obtained 0.550 g. (24.2%) of 3,4,6-tri-O-acetyl-2-deoxy-2-nicotinamido-1-O-nicotinoyl-β,D-glucopyranose of melting point 172°–173°C.

The tetraacetylglucopyranose used as the starting material can be prepared as follows:

24 G. of 2-amino-2-deoxy-1,3,4,6-tetra-O-acetyl-β,D-glucopyranose hydrochloride are dissolved in 150 ml. of pyridine and added to a mixture of 20 g. of nicotinic acid chloride hydrochloride in 150 ml. of pyridine. The mixture is stirred for 2 hours and then evaporated to dryness. The residue is taken up in 500 ml. of chloroform and washed with saturated sodium carbonate solution and saturated sodium chloride solution. The organic phase is dried over sodium sulfate and again evaporated. After crystallization from ethanol, there are obtained 29.5 g. of the desired tetraacetylglucopyranose of melting point 218°–219°C.

EXAMPLE 2

A solution of the anomers of 3,4,6-tri-O-acetyl-2-deoxy-2-nicotinamido-1-chloro-D-glucopyranose, obtained from 100 g. of N-nicotinoyl-D-glucosamine and 300 ml. of acetyl chloride, is diluted with 1.2 liters of methylene chloride and poured onto 1.2 liters of ice-water. The mixture is adjusted to pH 5–6 with a 2N sodium carbonate solution while stirring. The organic phase is separated, dried over magnesium sulfate and evaporated to dryness. The residue is dissolved in 500 ml. of acetonitrile, treated with a solution of the salt obtained from 70 g. of nicotinic acid and 150 ml. of triethylamine and stirred overnight. The solution is evaporated, taken up in 1 liter of chloroform, washed three times with 1.5 liters of water, dried over sodium sulfate and again evaporated. The residue is dissolved in 1.5 liters of ethanol, treated with 20 g. of active carbon, filtered under suction and evaporated to one-third of the original volume. After crystallization from alcoholic solution and two-fold recrystallization from ethanol, there are obtained 48 g. ( 26.5%) of 3,4,6-tri-O-acetyl-2-deoxy-2-nicotinamido-1-O-nicotinoyl-β,D-glucopyranose of melting point 175°–176°C.

EXAMPLE 3

A suspension of 10 g. of N-nicotinoyl-D-glucosamine in 30 ml. of propionyl chloride is stirred at room temperature for 18 hours and the resulting solution is evaporated to dryness. The residue is dissolved in 150 ml. of methylene chloride and poured onto 150 ml. of ice-water. The mixture obtained is adjusted to pH 7 with 2N sodium bicarbonate solution, the organic phase is dried over magnesium sulfate and the solution evaporated to dryness. A solution of the residue in 50 ml. of acetonitrile is treated with triethylammonium nicotinate (prepared from 6.5 g. of nicotinic acid and 15 ml. of triethylamine) and stirred at room temperature overnight. The mixture is evaporated, the residue taken up in 250 ml. of methylene chloride and the organic phase washed twice with 100 ml. of water, dried over magnesium sulfate and evaporated. After crystallization of the residue from ethyl acetate/isopropyl ether and recrystallization from isopropanol, there are obtained 3.3 g. (16.8%) of 3,4,6-tri-O-propionyl-2-deoxy-2-nicotinamido-1-O-nicotinoyl-β,D-glucopyranose of melting point 161°C.

EXAMPLE 4

0.5 G. of 1,3,4,6-tetra-O-benzoyl-2-deoxy-2-nicotinamido-β,D-glucopyranose (melting point 195°–196°C.) is dissolved in 5 ml. of methylene chloride saturated with hydrogen chloride. The solution is left to stand at room temperature for 24 hours. The solution is then evaporated to dryness, the residue dissolved in 20 ml. of methylene chloride and poured onto 10 ml. of ice-water. After adjusting the mixture to pH 7 with 2N sodium bicarbonate solution, the organic phase is dried over magnesium sulfate and evaporated to dryness. A solution of the residue in 10 ml. of acetonitrile is treated with triethylammonium nicotinate (prepared from 0.15 g. of nicotinic acid and 3 ml. of triethylamine) and stirred at room temperature overnight. The mixture is evaporated, the residue taken up in 25 ml. of methylene chloride and the organic phase washed twice with 10 ml. of water, dried over magnesium sulfate and evaporated. The residue is placed on a silica gel column (150 g.) and eluted with chloroform/ethanol (19:1). After crystallization and recrystallization of the pure product from ethanol, there is obtained 0.1 g. (20%) of 3,4,6-tri-O-benzoyl-2-deoxy-2-nicotinamido-1-O-nicotinoyl-β,D-glucopyranose of melting point 178°C.

The following example illustrates a typical pharmaceutical preparation containing one of the glucose derivatives provided by this invention.

EXAMPLE 5

Tablets of the following composition are prepared in the usual manner:

| | |
|---|---|
| 3,4,6-Tri-O-acetyl-2-deoxy-2-nicotinamido-1-O-nicotinoyl- β ,D-glucopyranose | 500 mg. |
| Citric acid | 5 mg. |
| Maize starch | 60 mg. |
| Microcrystalline cellulose | 120 mg. |
| Carboxymethylcellulose | 10 mg. |
| Magnesium stearate | 5 mg. |
| Total weight | 700 mg. |

We claim:
1. A glucose derivative of the formula

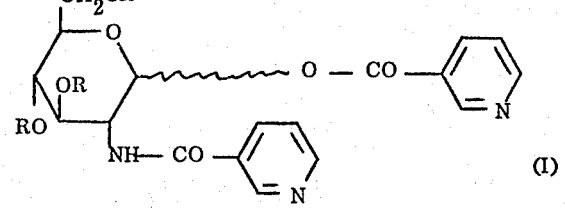

(I)

wherein R is lower alkanoyl, (lower alkoxy)-(lower alkanoyl) or benzoyl which may be substituted by $C_1$–$C_6$ alkyl, $C_1$–$C_6$ alkoxy or halogen.

2. The glucose derivative of claim 1 wherein R is lower alkanoyl.

3. The glucose derivative of claim 2 which is 3,4,6-tri-O-acetyl-2-deoxy-2-nicotinamido-1-O-nicotinoyl-β,D-glucopyranose.

4. The glucose derivative of claim 2 which is 3,4,6-tri-O-propionyl-2-deoxy-2-nicotinamido-1-O-nicotinoyl-β,D-glucopyranose.

5. A glucose derivative of claim 1 wherein R is benzoyl which may be substituted by $C_1$–$C_6$ alkyl, $C_1$–$C_6$ alkoxy or halogen.

6. The glucose derivative of claim 5 which is 3,4,6-tri-O-benzoyl-2-deoxy-2-nicotinamido-1-O-nicotinoyl-β,D-glucopyranose.

* * * * *